(12) United States Patent
Perkins et al.

(10) Patent No.: US 11,692,196 B2
(45) Date of Patent: Jul. 4, 2023

(54) METHODS FOR CREATING SYNTHETIC CHROMOSOMES EXPRESSING BIOSYNTHETIC PATHWAYS AND USES THEREOF

(71) Applicant: SynPloid Biotek, LLC, Savannah, GA (US)

(72) Inventors: Edward Perkins, Savannah, GA (US); Amy Greene, Savannah, GA (US)

(73) Assignee: CarryGenes Bioengineering, LLC, Savannah, GA (US)

( * ) Notice: Subject to any disclaimer, the term of this patent is extended or adjusted under 35 U.S.C. 154(b) by 781 days.

(21) Appl. No.: 16/092,837

(22) PCT Filed: Apr. 11, 2017

(86) PCT No.: PCT/US2017/027069
§ 371 (c)(1),
(2) Date: Oct. 11, 2018

(87) PCT Pub. No.: WO2017/180665
PCT Pub. Date: Oct. 19, 2017

(65) Prior Publication Data
US 2021/0403930 A1 Dec. 30, 2021

Related U.S. Application Data

(60) Provisional application No. 62/321,716, filed on Apr. 12, 2016.

(51) Int. Cl.
*C12N 15/81* (2006.01)
*C12N 15/85* (2006.01)

(52) U.S. Cl.
CPC ............ *C12N 15/81* (2013.01); *C12N 15/85* (2013.01)

(58) Field of Classification Search
None
See application file for complete search history.

(56) References Cited

U.S. PATENT DOCUMENTS

| | | |
|---|---|---|
| 2002/0160410 A1 | 10/2002 | Hadlaczky et al. |
| 2004/0096891 A1 | 5/2004 | Bennett |
| 2005/0181506 A1 | 8/2005 | Perkins et al. |
| 2007/0004002 A1 | 1/2007 | Okazaki |
| 2007/0077224 A1 | 4/2007 | Munn et al. |
| 2011/0318832 A1 | 12/2011 | Cech et al. |
| 2012/0064578 A1* | 3/2012 | Perkins .................. C12N 15/63 435/91.41 |
| 2012/0093785 A1 | 4/2012 | Oshimura et al. |
| 2014/0295501 A1 | 10/2014 | Katona et al. |
| 2015/0259684 A1 | 9/2015 | Church et al. |
| 2018/0010150 A1 | 1/2018 | Perkins et al. |

FOREIGN PATENT DOCUMENTS

| | | |
|---|---|---|
| EP | 2218786 A4 | 6/2011 |
| EP | 2522725 B1 | 10/2016 |
| EP | 1559782 B1 | 12/2016 |
| WO | 9740183 A2 | 10/1997 |
| WO | 0018941 A1 | 4/2000 |
| WO | 02096923 B1 | 5/2004 |
| WO | 2015066722 A1 | 5/2015 |

OTHER PUBLICATIONS

Lindenbaum et al., 2004, A mammalian artificial chromosome engineering system (ACE System) applicable to biopharmaceutical protein production, transgenesis and gene-based cell therapy. Nucleic Acids Research, 2004, vol. 32, No. 21 e172. p. 1-15.*
Nakazawa, Yozo. "Gene-modified T-cell Therapy using Chimeric Antigen Receptor." Shinshu Medical Journal, 2013, 61:197-203. (In Japanese, with partial translation of Introduction in left col. of p. 197, and IV in right col. of p. 199).
Basu, J., "Artificial and Engineered Chromosomes: Non-Integrating Vectors for Gene Therapy." Trends in Molecular Medicine, Elsevier Current Trends, vol. 11 (5), pp. 251-258 (2005).
European Search Report dated Oct. 22, 2019 in EP17783010.6, based on PCT/US17/27069 filed Apr. 11, 2017.
Ikeno, M et al., "Construction of YAC-based mammalian artificial chromosomes", Nature Biotechnology, (19980500), vol. 16, No. 5, pp. 431-439, XP009060040.
International Search Report dated Apr. 10, 2017 in PCT/US17/27069.
Ishihara, et al., 2007, Metabolomics, Kluwer Academic Publishers-Plenum Publishers, NL, vol. 3(3):319-334.
Katoh, et al., (2004) "Construction of a novel human artificial chromosome vector for gene delivery." Biochem. Biophys. Res. Comm. 321:280-290.
Kazuki, et al., "Refined human artificial chromosome vectors for gene therapy and animal transgenesis." Gene Therapy, vol. 18(4):384-393 (2010).
Kazuki, Y et al., "Human Artificial Chromosomes for Gene Delivery and the Development of Animal Models", Molecular Therapy, (2011) 19(9):1591-1601. doi:10.1038/mt.2011.136, XP055581607.
Kouprina et al., (2013) "A new generation of human artificial chromosomes for functional genomics and gene therapy", Cell Mol Life Sci., vol. 70, No. 7, pp. 1135-1148, XP055470579.
Kouprina, et al., (2014) "Human Artificial Chromosome-Based Gene Delivery Vectors for Biomedicine and Biotechnology." Expert Opinion on Drug Delivery. 11(4):517-535.
Kurosaki, et al., "Integration-free and stable expression of FVIII using a human artificial chromosome." Journal of Human Genetics, vol. 56 (10), pp. 727-733 (2011).
Lindenbaum et al., "A mammalian artificial chromosome engineering system (ACE System) applicable to biopharmaceutical protein production, transgenesis and gene-based cell therapy," Nucleic Acids Research, (2004), vol. 32, No. 21, pp. 1-15 (p. e172, XP002741726).

(Continued)

*Primary Examiner* — Maria G Leavitt
(74) *Attorney, Agent, or Firm* — Susan Myers Fitch

(57) ABSTRACT

The present invention encompasses compositions and methods to allow one to deliver and express multiple genes from a biosynthetic pathway in a recipient cell via a synthetic chromosome.

12 Claims, 3 Drawing Sheets
Specification includes a Sequence Listing.

(56) References Cited

OTHER PUBLICATIONS

Martella, et al., "Mammalian Synthetic Biology: Time for Big Macs." ACS Synthetic Biology, vol. 5 (10), pp. 1040-1049 (2016).
Naesby, et al., 2009, "Yeast artificial chromosomes employed for random assembly of biosynthetic pathways and production of diverse compounds in *Saccharomyces cerevisiae*." Microbial Cell Factories, vol. 8(1):45 (2009).
Ren, X et al., "A Novel Human Artificial Chromosome Vector Provides Effective Cell Lineage-Specific Transgene Expression in Human Mesenchymal Stem Cells", Stem Cells, (Nov. 1, 2005), vol. 23, No. 10, doi:10.1634/stemcells.2005-0021, pp. 1608-1616, XP055473399.
Rocchi, et al., (2010) "*Escherichia coli*-Cloned CTFR Loci Relevant for Human Artificial Chromosome Therapy." Human Gene Therapy, 21:1077-1092.
Shitara, et al., 2008, "Telomerase-mediated life-span extension of human primary fibroblasts by human artificial chromosome (HAC) vector." Biochem. Biophys. Res. Commun. 369(3):807-11.
Siuti et al., "Synthetic circuits integrating logic and memory in living cells," Nature Biotechnology, (2013), vol. 31, No. 5, pp. 448-452.
Suzuki, et al., (2014), "A Novel System for Simultaneous or Sequential Integration of Multiple Gene-Loading Vectors into a Defined Site of a Human Artificial Chromosome." Plos One. 9(10), pp. 1-9 (2014).
Takiguchi, et al., "A Novel and Stable Mouse Artificial Chromosome Vector." ACS Synthetic Biology, vol. 3 (12), pp. 903-914 (2014).
Toth, et al., "Novel Method to Load Multiple Genes onto a Mammalian Artificial Chromosome." Plos One, Public Library of Science, US, vol. 9 (1), pp. e85565-1 (2014).
Vanderbyl, S et al., "Transfer and Stable Transgene Expression of a Mammalian Artificial Chromosome into Bone Marrow-Derived Human Mesenchymal Stem Cells", Stem Cells, (20040500), vol. 22, No. 3, doi:doi:10.1634/stemcells.22-3-324, pp. 324-333, XP002506658.
Yamaguchi, et al., 2011 "A Method for Producing Transgenic Cells Using a Multi-Integrase System on a Human Artificial Chromosome Vector." PLoS ONE 6(2): e17267, https://doi.org/10.1371/journal.pone.0017267.
Yu, et al., "Plant artificial chromosome technology and its potential application in genetic engineering." Plant Biotechnology Journal, vol. 14(5):1174-1182 (2015).
Brenda Grimes and Zoia Monaco, "Artificial and Engineered Chromosomes: Developments and Prospects for Gene Therapy," Chromosoma, (2005), 114:230-241.
Bruce Bunnell, et al., "Development of Mammalian Artificial Chromosomes for the Treatment of Genetic Diseases Sandhoff and Krabbe Diseases," Expert Opin. Biol. Therapy (2005) 5(2):95-206.
Tomohiro Tsuduki, et al., "An Artificially Constructed De Novo Human Chromosome Behaves Almost Identically to Its Natural Counterpart during Metaphase and Anaphase in Living Ceils," Molecular and Cellular Biology (2006), vol. 26, No. 20, p. 7682-7695.
Yueju Wang, et al., "Recombinase Technology: Applications and Possibilities," Plant Cell Rep., (2011), 30:267-285.

\* cited by examiner

SEQUENCE LISTING

<160> NUMBER OF SEQ ID NOS: 10

<210> SEQ ID NO 1
<211> LENGTH: 57
<212> TYPE: DNA
<213> ORGANISM: Artificial Sequence
<220> FEATURE:
<223> OTHER INFORMATION: self cleaving sequence

<400> SEQUENCE: 1
gctactaact tcagcctgct gaagcaggct ggagacgtgg aggagaaccc tggacct        57

<210> SEQ ID NO 2
<211> LENGTH: 54
<212> TYPE: DNA
<213> ORGANISM: Artificial Sequence
<220> FEATURE:
<223> OTHER INFORMATION: self cleaving sequence

<400> SEQUENCE: 2
gagggcagag gaagtctgct aacatgcggt gacgtcgagg agaatcctgg acct           54

<210> SEQ ID NO 3
<211> LENGTH: 60
<212> TYPE: DNA
<213> ORGANISM: Artificial Sequence
<220> FEATURE:
<223> OTHER INFORMATION: self cleaving sequence

<400> SEQUENCE: 3
cagtgtacta attatgctct cttgaaattg gctggagatg ttgagagcaa ccctggacct     60

<210> SEQ ID NO 4
<211> LENGTH: 66
<212> TYPE: DNA
<213> ORGANISM: Artificial Sequence
<220> FEATURE:
<223> OTHER INFORMATION: self cleaving sequence

<400> SEQUENCE: 4
gtgaaacaga ctttgaattt tgaccttctc aagttggcgg gagacgtgga gtccaaccct     60
ggacct                                                               66

<210> SEQ ID NO 5
<211> LENGTH: 24
<212> TYPE: DNA
<213> ORGANISM: Artificial Sequence
<220> FEATURE:
<223> OTHER INFORMATION: ligation junction

<400> SEQUENCE: 5
accgagctgc aagaactctt cctc                                           24

<210> SEQ ID NO 6
<211> LENGTH: 18
<212> TYPE: DNA
<213> ORGANISM: Artificial Sequence
<220> FEATURE:
<223> OTHER INFORMATION: ligation junction

<400> SEQUENCE: 6
ctcgccgcag ccgtgtaa                                                  18

<210> SEQ ID NO 7
<211> LENGTH: 22

```
<212> TYPE: DNA
<213> ORGANISM: Artificial Sequence
<220> FEATURE:
<223> OTHER INFORMATION: ligation junction

<400> SEQUENCE: 7
gcgctaatgc tctgttacag gt                                              22

<210> SEQ ID NO 8
<211> LENGTH: 20
<212> TYPE: DNA
<213> ORGANISM: Artificial Sequence
<220> FEATURE:
<223> OTHER INFORMATION: ligation junction

<400> SEQUENCE: 8
ggaaagctgc cagtgccttg                                                 20

<210> SEQ ID NO 9
<211> LENGTH: 53
<212> TYPE: DNA
<213> ORGANISM: Artificial Sequence
<220> FEATURE:
<223> OTHER INFORMATION: lox cassette

<400> SEQUENCE: 9
agccgtgtaa ccgagcatag tgaagcctgc tttttatac taacttgagc gaa             53

<210> SEQ ID NO 10
<211> LENGTH: 43
<212> TYPE: DNA
<213> ORGANISM: Artificial Sequence
<220> FEATURE:
<223> OTHER INFORMATION: lox cassette

<400> SEQUENCE: 10
ctgtttcctt cagcctgcat ggccttgact agagggtcga cgg                       43
```

METHODS FOR CREATING SYNTHETIC CHROMOSOMES EXPRESSING BIOSYNTHETIC PATHWAYS AND USES THEREOF

CROSS REFERENCE TO RELATED APPLICATIONS

This International PCT application claims priority to US Provisional Patent Application No. 62/321,716 filed Apr. 12, 2016.

REFERENCE TO SEQUENCE LISTING, TABLE OR COMPUTER PROGRAM

A sequence listing, 2330 kilobytes in size, entitled "SYNP-004_ST25.txt" and created on Jul. 6, 2020 is included and incorporated by reference in the present application, and contains the same information included in the specification as filed on Oct. 11, 2018, as well as in PCT application PCT/US17/27069 filed Apr. 11, 2017.

STATEMENT REGARDING GOVERNMENT SUPPORT

This invention was made with the support of the United States Government under contract D15PC00008 awarded by DARPA. The U.S. Government has certain rights in this invention.

FIELD OF THE INVENTION

The field of the invention encompasses methods to allow one to engineer synthetic chromosomes to deliver multiple genes from a biosynthetic pathway to a recipient cell.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Current methods for engineering cells to incorporate and express multiple genes that, e.g., confer on the cells the ability to produce cellular metabolites such as amino acids, nucleic acids, glycoproteins and the like are reliant on either viral-based or plasmid-based nucleic acid delivery technology. Often, however, a cell's ability to produce such metabolites requires the expression and functional orchestration of multiple gene products that make up the biochemical pathway for metabolite synthesis. For example, many mammalian cells lack the necessary enzymes required to make essential amino acids. To enable cells to make these amino acids, cells must be engineered to express heterologous genes found in fungi or bacteria; however, due to the limited payload capacity of viral and plasmid nucleic acid vector delivery systems, multiple iterations of transfection or transduction events are necessary in order to generate an entire biochemical or biosynthetic pathway in the recipient cells.

The ability to generate fully-functional mammalian synthetic chromosomes represents a powerful system for cell-based correction of genetic disorders and production of biological pathways. Fully-functional mammalian synthetic chromosomes offer several advantages over bacterial-based and viral-based delivery systems including increased payload size, the fact that extrachromosomal maintenance avoids potential host-cell disruption, avoidance of transcriptional silencing of introduced genes and possible immunological complications, and mammalian synthetic chromosomes can be derived from and tailored to the species into which the synthetic chromosome is to be inserted. There is a need in the art for compositions and methods that allow one to deliver and express multiple genes from a biosynthetic pathway in cells to produce metabolites. The present invention provides methods and compositions that address this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description, including those aspects illustrated in the accompanying drawings and defined in the appended claims.

The present invention encompasses compositions and methods for delivering and expressing multiple genes from one or more biosynthetic pathways in a recipient cell via a synthetic chromosome. Pathways may include 1) those known to produce a specific end product; 2) a novel pathway created by incorporating existing genes in a novel combination and/or expressing existing genes in a novel cell type to produce a specific end product that may be novel to the cell type in which the end product is produced; or 3) a novel pathway created by incorporating novel genes alone or in combination with existing genes to produce a novel end product.

Thus, in one embodiment, the methods of the present invention provide a method for constructing a biosynthetic pathway in a recipient cell comprising: transfecting the recipient cell line with synthetic chromosome production components including nucleic acid sequences that allow for site-specific integration of target nucleic acid sequences; producing a synthetic platform chromosome with multiple site-specific recombination sites; transfecting the recipient cell line with a delivery vector comprising multiple genes capable of effectuating a biosynthetic pathway, wherein the delivery vector comprises at least one site-specific recombination site; activating site-specific recombination between the synthetic platform chromosome and the delivery vector, wherein the multiple genes capable of effectuating a biosynthetic pathway are loaded onto the synthetic platform chromosome to produce a synthetic chromosome expressing the biosynthetic pathway; and isolating a recipient cell comprising the synthetic chromosome expressing the biosynthetic pathway.

In some aspects of this embodiment, the multiple genes capable of effectuating a biosynthetic pathway comprise genes necessary for tryptophan biosynthesis, and in some aspects, the genes necessary for tryptophan biosynthesis comprise the five genes necessary for synthesis of tryptophan in *Saccharomyces cerevisiae*.

In some aspects of this embodiment, in addition to delivering the multiple genes capable of effectuating a biosynthetic pathway, the delivery vector further comprises one or more of a) one or more genes that interfere with or block tumor cell ability to inhibit immune cell cycle progression, b) one or more genes that code for factors that enhance immune cell activation and growth, or c) one or more genes that increase specificity of immune cells to developing tumors.

In yet other aspects of this embodiment, the method further comprises the steps of: isolating the synthetic chromosome expressing the biosynthetic pathway; and transferring the synthetic chromosome to a second recipient cell. In some aspects, the second recipient cell is selected from a universal donor T-cell or a patient autologous T-cell. Other aspects of the invention provide the synthetic chromosome expressing the biosynthetic pathway, and yet other aspects provide the second recipient cell.

In some aspects of the invention, the nucleic acid sequences that allow for site-specific integration comprise attP, attB, attL, and attR or mutated versions of attP, attB, attL, and attR.

Other embodiments of the invention further comprise the steps of transfecting the recipient cell line with a second delivery vector comprising multiple genes capable of effectuating a second biosynthetic pathway, wherein the second delivery vector comprises at least one site-specific recombination site; activating site-specific recombination between the synthetic platform chromosome and the second delivery vector, wherein the multiple genes capable of effectuating a second biosynthetic pathway are loaded onto the synthetic platform chromosome to produce a synthetic chromosome expressing the second biosynthetic pathway; and isolating a recipient cell comprising the synthetic chromosome expressing the second biosynthetic pathway. Some aspects of this embodiment further comprise the steps of isolating the synthetic chromosome expressing the second biosynthetic pathway; and transferring the synthetic chromosome expressing the second biosynthetic pathway to a second recipient cell.

These and other aspects and uses of the invention will be described in the detailed description.

DETAILED DESCRIPTION OF THE INVENTION

Figure 1:
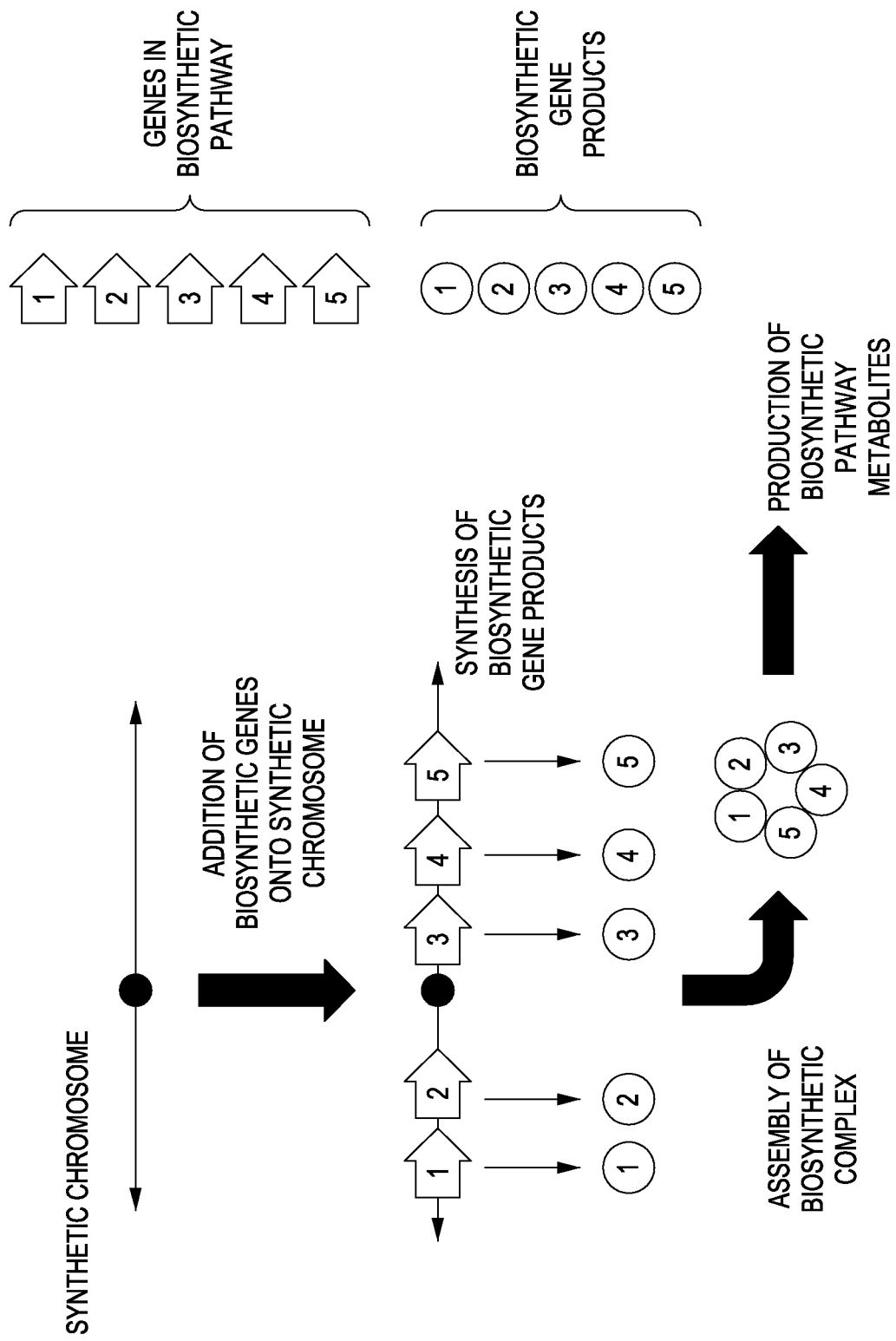
FIG. 1 is a simplified schematic of one embodiment of the methods of the present invention where cellular physiology is augmented by production of biosynthetic pathway metabolites from a synthetic chromosome.

The methods described herein may employ, unless otherwise indicated, conventional techniques and descriptions of molecular biology (including recombinant techniques), cell biology, biochemistry, and cellular engineering technology, all of which are within the skill of those who practice in the art. Such conventional techniques include oligonucleotide synthesis, hybridization and ligation of oligonucleotides, transformation and transduction of cells, engineering of recombination systems, creation of transgenic animals and plants, and human gene therapy. Specific illustrations of suitable techniques can be had by reference to the examples herein. However, equivalent conventional procedures can, of course, also be used. Such conventional techniques and descriptions can be found in standard laboratory manuals such as *Genome Analysis: A Laboratory Manual Series* (Vols. I-IV) (Green, et al., eds., 1999); *Genetic Variation: A Laboratory Manual* (Weiner, et al., eds., 2007); Sambrook and Russell, *Condensed Protocols from Molecular Cloning: A Laboratory Manual* (2006); and Sambrook and Russell, *Molecular Cloning: A Laboratory Manual* (2002) (all from Cold Spring Harbor Laboratory Press); *Protein Methods* (Bollag et al., John Wiley & Sons 1996); *Nonviral Vectors for Gene Therapy* (Wagner et al. eds., Academic Press 1999); *Viral Vectors* (Kaplift & Loewy, eds., Academic Press 1995); *Immunology Methods Manual* (Lefkovits ed., Academic Press 1997); *Gene Therapy Techniques, Applications and Regulations From Laboratory to Clinic* (Meager, ed., John Wiley & Sons 1999); M. Giacca, *Gene Therapy* (Springer 2010); *Gene Therapy Protocols* (LeDoux, ed., Springer 2008); *Cell and Tissue Culture: Laboratory Procedures in Biotechnology* (Doyle & Griffiths, eds., John Wiley & Sons 1998); *Mammalian Chromosome Engineering—Methods and Protocols* (G. Hadlaczky, ed., Humana Press 2011); *Essential Stem Cell Methods*, (Lanza and Klimanskaya, eds., Academic Press 2011); *Stem Cell Therapies: Opportunities for Ensuring the Quality and Safety of Clinical Offerings: Summary of a Joint Workshop* (Board on Health Sciences Policy, National Academies Press 2014); *Essentials of Stem Cell Biology*, Third Ed., (Lanza and Atala, eds., Academic Press 2013); and *Handbook of Stem Cells*, (Atala and Lanza, eds., Academic Press 2012), all of which are herein incorporated by reference in their entirety for all purposes. Before the present compositions, research tools and methods are described, it is to be understood that this invention is not limited to the specific methods, compositions, targets and uses described, as such may, of course, vary. It is also to be understood that the terminology used herein is for the purpose of describing particular aspects only and is not intended to limit the scope of the present invention, which will be limited only by the appended claims.

Note that as used in the present specification and in the appended claims, the singular forms "a," "and," and "the" include plural referents unless the context clearly dictates otherwise. Thus, for example, reference to "a composition" refers to one or mixtures of compositions, and reference to "an assay" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, formulations and methodologies which are described in the publication and which might be used in connection with the presently described invention.

Where a range of values is provided, it is understood that each intervening value between the upper and lower limit of that range and any other stated or intervening value in that stated range is encompassed within the invention. The upper and lower limits of these smaller ranges may independently be included in the smaller ranges, subject to any specifically excluded limit in the stated range. Where the stated range includes both of the limits, ranges excluding only one of those included limits are also included in the invention.

In the following description, numerous specific details are set forth to provide a more thorough understanding of the present invention. However, it will be apparent to one of ordinary skill in the art upon reading the specification that the present invention may be practiced without one or more of these specific details. In other instances, well-known features and procedures well known to those skilled in the art have not been described in order to avoid obscuring the invention.

Definitions

Unless expressly stated, the terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated.

"Binding" as used herein (e.g., with reference to an nucleic acid-binding domain of a polypeptide) refers to a non-covalent interaction between a polypeptide and a nucleic acid. While in a state of non-covalent interaction, the polypeptide and nucleic acid are said to be "associated", "interacting", or "binding". Binding interactions are generally characterized by a dissociation constant (Kd) of less than $10^{-6}$ M to less than $10^{-15}$ M. "Affinity" refers to the strength of binding, increased binding affinity being correlated with a lower Kd.

By "binding domain" it is meant a polypeptide or protein domain that is able to bind non-covalently to another molecule. A binding domain can bind to, for example, a DNA molecule (a DNA-binding protein), an RNA molecule (an RNA-binding protein) and/or a protein molecule (a protein-binding protein).

A "centromere" is any nucleic acid sequence that confers an ability of a chromosome to segregate to daughter cells through cell division. A centromere may confer stable segregation of a nucleic acid sequence, including a synthetic chromosome containing the centromere, through mitotic and meiotic divisions. A centromere does not necessarily need to be derived from the same species as the cells into which it is introduced, but preferably the centromere has the ability to promote DNA segregation in cells of that species. A "dicentric" chromosome is a chromosome that contains two centromeres. A "formerly dicentric chromosome" is a chromosome that is produced when a dicentric chromosome fragments. A "chromosome" is a nucleic acid molecule—and associated proteins—that is capable of replication and segregation in a cell upon division of the cell. Typically, a chromosome contains a centromeric region, replication origins, telomeric regions and a region of nucleic acid between the centromeric and telomeric regions. An "acrocentric chromosome" refers to a chromosome with arms of unequal length.

A "coding sequence" or a sequence that "encodes" a peptide is a nucleic acid molecule that is transcribed (in the case of DNA) and translated (in the case of mRNA) into a polypeptide in vivo when placed under the control of appropriate control sequences. The boundaries of the coding sequence typically are determined by a start codon at the 5' (amino) terminus and a translation stop codon at the 3' (carboxy) terminus.

The term DNA "control sequences" refers collectively to promoter sequences, polyadenylation signals, transcription termination sequences, upstream regulatory domains, origins of replication, internal ribosome entry sites, enhancers, and the like, which collectively provide for the replication, transcription and translation of a coding sequence in a recipient cell. Not all of these types of control sequences need to be present so long as a selected coding sequence is capable of being replicated, transcribed and translated in an appropriate host cell.

The term "effectuating" a biosynthetic pathway refers to recapitulating a known biosynthetic pathway as well as creating and executing a novel biosynthetic pathway.

"Endogenous chromosomes" refer to chromosomes found in a cell prior to generation or introduction of a synthetic chromosome.

As used herein, "euchromatin" refers to chromatin that stains diffusely and that typically contains genes, and "heterochromatin" refers to chromatin that remains unusually condensed and is thought to be transcriptionally inactive. Highly repetitive DNA sequences (satellite DNA) are usually located in regions of the heterochromatin surrounding the centromere.

The terms "heterologous DNA" or "foreign DNA" (or "heterologous RNA" or "foreign RNA") are used interchangeably and refer to DNA or RNA that does not occur naturally as part of the genome in which it is present, or is found in a location or locations and/or in amounts in a genome or cell that differ from that in which it occurs in nature. Examples of heterologous DNA include, but are not limited to, DNA that encodes a gene product or gene product(s) of interest. Other examples of heterologous DNA include, but are not limited to, DNA that encodes traceable marker proteins as well as regulatory DNA sequences.

As used herein, the term "metabolite" refers to natural metabolites (such as, for example, cholesterol), heterologous metabolites (such as, for example, tryptophan in humans), engineered metabolites (i.e., novel, man-made metabolites such as chimeric proteins or engineered RNA interference molecules) or any other metabolite that confers upon a cell an altered function by, e.g., enhancing or inhibiting a biosynthetic pathway.

"Operably linked" refers to an arrangement of elements where the components so described are configured so as to perform their usual function. Thus, control sequences operably linked to a coding sequence are capable of effecting the expression of the coding sequence. The control sequences need not be contiguous with the coding sequence so long as they function to direct the expression of the coding sequence. Thus, for example, intervening untranslated yet transcribed sequences can be present between a promoter sequence and the coding sequence and the promoter sequence can still be considered "operably linked" to the coding sequence. In fact, such sequences need not reside on the same contiguous DNA molecule (i.e. chromosome), and may still have interactions resulting in altered regulation.

A "promoter" or "promoter sequence" is a DNA regulatory region capable of binding RNA polymerase in a cell and initiating transcription of a polynucleotide or polypeptide coding sequence such as messenger RNA, ribosomal RNAs, small nuclear or nucleolar RNAs or any kind of RNA transcribed by any class of any RNA polymerase I, II or III.

A recipient cell is a cell into which the components for creating a synthetic chromosome, a synthetic platform chromosome or a synthetic platform chromosome bioengineered to contain a given set of DNA elements. Types of recipient cell may include but are not limited to: stem cells, mesenchymal stem cells, adult derived stem cells, T-cells, immune cells, induced pluripotent stem cells, fibroblasts, endothelial cells, cells of the mesoderm, ectoderm and endoderm. Also included would be tumor cells cell culture lines, primary cells, and germ cells. The cells can then be, e.g., cultured, prepared for transplantation, used to create whole transgenic animals, and the like.

"Recognition sequences" are particular sequences of nucleotides that a protein, DNA, or RNA molecule, or combinations thereof (such as, but not limited to, a restriction endonuclease, a modification methylase or a recombinase) recognizes and binds. For example, a recognition sequence for Cre recombinase is a 34 base pair sequence containing two 13 base pair inverted repeats (serving as the recombinase binding sites) flanking an 8 base pair core and designated loxP (see, e.g., Sauer, Current Opinion in Biotechnology, 5:521-527 (1994)). Other examples of recognition sequences, include, but are not limited to, attB and attP, attR and attL and others that are recognized by the recombinase enzyme bacteriophage Lambda Integrase. The recombination site designated attB is an approximately 33 base pair sequence containing two 9 base pair core-type Int binding sites and a 7 base pair overlap region; attP is an approximately 240 base pair sequence containing core-type Int binding sites and arm-type Int binding sites as well as sites for auxiliary proteins IHF, FIS, and Xis (see, e.g., Landy, Current Opinion in Biotechnology, 3:699-7071 (1993)).

A "recombinase" is an enzyme that catalyzes the exchange of DNA segments at specific recombination sites. An integrase refers to a recombinase that is usually derived from viruses or transposons, as well as perhaps ancient viruses. "Recombination proteins" include excisive proteins, integrative proteins, enzymes, co-factors and associated proteins that are involved in recombination reactions using one or more recombination sites (see, Landy, Current Opinion in Biotechnology, 3:699-707 (1993)). The recombination proteins used in the methods herein can be delivered to a cell via an expression cassette on an appropriate vector, such as a plasmid, and the like. In other embodiments, recombination proteins can be delivered to a cell in protein form in the same reaction mixture used to deliver the desired nucleic acid(s). In yet other embodiments, the recombinase could also be encoded in the cell and expressed upon demand using a tightly controlled inducible promoter.

"Ribosomal RNA" (rRNA) is the specialized RNA that forms part of the structure of a ribosome and participates in the synthesis of proteins. Ribosomal RNA is produced by transcription of genes which, in eukaryotic cells, are present in multiple copies. In human cells, the approximately 250 copies of rRNA genes (i.e., genes which encode rRNA) per haploid genome are spread out in clusters on at least five different chromosomes (chromosomes 13, 14, 15, 21 and 22). In human cells, multiple copies of the highly conserved rRNA genes are located in a tandemly arranged series of rDNA units, which are generally about 40-45 kb in length and contain a transcribed region and a nontranscribed region known as spacer (i.e., intergenic spacer) DNA which can vary in length and sequence.

As used herein the term "selectable marker" refers to a gene introduced into a cell, particularly in the context of this invention into cells in culture, that confers a trait suitable for artificial selection. General use selectable markers are well-known to those of ordinary skill in the art. In preferred embodiments, selectable markers for use in a human synthetic chromosome system should be non-immunogenic in the human and include, but are not limited to: human nerve growth factor receptor (detected with a MAb, such as described in U.S. Pat. No. 6,365,373); truncated human growth factor receptor (detected with MAb); mutant human dihydrofolate reductase (DHFR; fluorescent MTX substrate available); secreted alkaline phosphatase (SEAP; fluorescent substrate available); human thymidylate synthase (TS; confers resistance to anti-cancer agent fluorodeoxyuridine); human glutathione S-transferase alpha (GSTA 1; conjugates glutathione to the stem cell selective alkylator busulfan; chemoprotective selectable marker in CD34$^+$cells); CD24 cell surface antigen in hematopoietic stem cells; human CAD gene to confer resistance to N-phosphonoacetyl-L-aspartate (PALA); human multi-drug resistance-1 (MDR-1; P-glycoprotein surface protein selectable by increased drug resistance or enriched by FACS); human CD25 (IL-2α; detectable by Mab-FITC); Methylguanine-DNA methyltransferase (MGMT; selectable by carmustine); and Cytidine deaminase (CD; selectable by Ara-C). Drug selectable markers such as puromycin, hygromycin, blasticidin, G418, tetracycline may also be employed. In addition, using FACs sorting, any fluorescent marker gene may be used for positive selection, as may chemiluminescent markers (e.g. Halotags), and the like.

"Site-specific recombination" refers to site-specific recombination that is effected between two specific sites on a single nucleic acid molecule or between two different molecules that requires the presence of an exogenous protein, such as an integrase or recombinase. Certain site-specific recombination systems can be used to specifically delete, invert, or insert DNA, with the precise event controlled by the orientation of the specific sites, the specific system and the presence of accessory proteins or factors. In addition, segments of DNA can be exchanged between chromosomes (chromosome arm exchange).

"Synthetic chromosomes" (also referred to as "artificial chromosomes") are nucleic acid molecules, typically DNA molecules, that have the capacity to accommodate and express heterologous genes and that stably replicate and segregate alongside endogenous chromosomes in cells. A "mammalian synthetic chromosome" refers to chromosomes that have an active mammalian centromere(s). A "human synthetic chromosome" refers to a chromosome that includes a centromere that functions in human cells and that preferably is produced in human cells. For exemplary artificial chromosomes, see, e.g., U.S. Pat. Nos. 8,389,802; 7,521,240; 6,025,155; 6,077,697; 5,891,691; 5,869,294; 5,721,118; 5,712,134; 5,695,967; and 5,288,625 and published International PCT application Nos, WO 97/40183 and WO 98/08964.

The terms "subject", "individual" or "patient" may be used interchangeably herein and refer to a mammal, and in some embodiments, a human.

A "vector" is a replicon, such as plasmid, phage, viral construct, cosmid, bacterial artificial chromosome, P-1 derived artificial chromosome or yeast artificial chromosome to which another DNA segment may be attached. In some instances a vector may be a chromosome such as in the case of an arm exchange from one endogenous chromosome engineered to comprise a recombination site to a synthetic chromosome. Vectors are used to transduce and express a DNA segment in cell.

The Invention

The present invention encompasses compositions and methods to allow one to deliver and express multiple genes from a biosynthetic pathway in cells to produce metabolites. Synthetic chromosomes with their large carrying capacity can carry and express multiple gene products—in particular, multiple genes from one or more biosynthetic pathways—thereby circumventing the limitations of viral- and plasmid-based nucleic acid delivery. The present invention provides methods and compositions to allow for production of a metabolite (or more than one metabolite) whose synthesis requires the coordinated expression and function of multiple genes in a biochemical pathway, thereby augmenting and enhancing the cellular physiology of the recipient cell. Pathways may include 1) those known to produce a specific end product; 2) a novel pathway created by incorporating existing genes in a novel combination and/or expressing existing genes in a novel cell type to produce a specific end product that may be novel to the cell type in which the end product is produced; or 3) a novel pathway created by incorporating novel genes alone or in combination with existing genes to produce a novel end product. Thus, the methods and compositions of the present invention allow for engineering of cells to synthesize a metabolite that is absent or synthesized at a sub-optimal level in the cells, and is applicable to all methodologies of synthetic chromosome production, including the "top down" approach, the "bottom up" approach, engineering of naturally-occurring minichromosomes, and induced de novo chromosome generation by targeted amplification of specific chromosomal segments (all of which are discussed in more detail, infra).

FIG. 1 is a simplified schematic of one embodiment of the methods of the present invention for functionally enhancing the biosynthetic capabilities of cells. FIG. 1 shows a synthetic platform chromosome resident in a cell. A delivery vector carrying the genes of a biosynthetic pathway is delivered to the cell, and genes from the biosynthetic pathway are "loaded onto" the synthetic platform chromosome (described in more detail infra). The genes that have been loaded onto the synthetic chromosome are then expressed in the cell. The proteins expressed from the transcription and translation of the genes from the synthetic chromosome then act in concert to produce one or more metabolites through a biosynthetic complex (i.e., a series of enzymatic reactions).

An example of the utility of employing a synthetic platform chromosome for cellular functional enhancement is the engineering of immune system cells to synthesize the essential amino acid tryptophan. During tumor growth, tumor cells import large amounts of tryptophan from the local tumor environment leading to the starvation and subsequent arrest of immune cells that inhibit tumor cell growth, rendering the starved immune cells incapable of inhibiting the growing tumor cells. Tryptophan is an essential amino acid—that is, an amino acid that cannot be synthesized de novo by humans—and dietary intake of tryptophan cannot mitigate the tryptophan starvation induced by the tumor cells. However, immune cells containing a synthetic chromosome expressing heterologous genes that lead to tryptophan biosynthesis have a selective advantage and escape "tryptophan-less" death during interaction with the tumor cells or in the tumor cell environment. For example, the yeast *Saccharomyces cerevisiae* expresses five genes necessary for synthesis of tryptophan (TRP1-5). Each of these genes can be isolated and controlled from mammalian promotors (either constitutively expressed or expressed from a regulatable promoter) and placed onto a bacterial vector that can carry large amounts of DNA such as a Bacterial Artificial Chromosome (BAC) that is engineered to deliver or "load" the multiple genes onto a synthetic platform chromosome (described infra). The synthetic chromosome comprising the tryptophan biosynthesis genes may then subsequently be introduced into immune cells (e.g., universal donor T-cells or patient autologous T-cells) for immuno-oncology cell-based therapy.

In addition to conferring resistance to "tryptophan-less" death, the large carrying capacity of the synthetic chromosome additionally permits engineering of genes for other biosynthetic pathways that block tumor cell inhibition, including but not limited to 1) expression of genes that interfere with or block the tumor cells' ability to inhibit immune cell cycle progression, e.g., anti-PD-1 (programmed cell death protein 1) or anti-CTLA-4 (central T-Cell activation and inhibition 4) molecules; 2) factors that enhance immune cell activation and growth (e.g., Interleukin-2 or other such cytokines); and/or 3) factors that increase specificity of the engineered immune cells to developing tumors, e.g., addition of factors that increase immune cell homing to tumors or immune cell binding to specific tumor markers. Thus, the engineering of the tryptophan biochemical pathway along with additional pathways and/or factors demarcates a synthetic platform chromosome for immune cell-based anti-cancer therapeutics (that is, an "immuno/onc synthetic chromosome or immuno/onc SynC").

Synthetic Chromosome Production

Synthetic chromosomes are created in cultured cells. In some embodiments, the cells to be engineered and/or produce the synthetic chromosome can be cells that naturally occur in a subject (human patient, animal or plant) in which the genes or regulatory sequences from the synthetic chromosome will ultimately be expressed. Such cells can be primary-culture cell lines established for the purpose of synthetic chromosome production specific for an individual. In other embodiments, the cells to be engineered and/or produce the synthetic chromosome are from an established cell line. A wide variety of cell lines for tissue culture are known in the art. Examples of cell lines include but are not limited to human cells lines such as 293-T (embryonic kidney), 721 (melanoma), A2780 (ovary), A172 (glioblastoma), A253 (carcinoma), A431 (epithelium), A549 (carcinoma), BCP-1 (lymphoma), BEAS-2B (lung), BR 293 (breast), BxPC3 (pancreatic carcinoma), Cal-27 (tongue), COR-L23 (lung), COV-434 (ovary), CML T1 (leukemia), DUI45 (prostate), DuCaP (prostate), FM3 (lymph node), H1299 (lung), H69 (lung), HCA2 (fibroblast), HEK0293 (embryonic kidney), HeLa (cervix), HL-60 (myeloblast), HMEC (epithelium), HT-29 (colon), HUVEC (umbilical vein epithelium), Jurkat (T cell leukemia), JY (lymphoblastoid), K562 (lymphoblastoid), KBM-7 (lymphoblastoid), Ku812 (lymphoblastoid), KCL22 (lymphoblastoid), KGI (lymphoblastoid), KYO1 (lymphoblastoid), LNCap (prostate), Ma-Mel (melanoma), MCF-7 (mammary gland), MDF-10A (mammary gland), MDA-MB-231, -468 and -435 (breast), MG63 (osteosarcoma), MOR/0.2R (lung), MONO-MAC6 (white blood cells), MRCS (lung), NCI-H69 (lung), NALM-1 (peripheral blood), NW-145 (melanoma), OPCN/OPCT (prostate), Peer (leukemia), Raji (B lymphoma), Saos-2 (osteosarcoma), Sf21 (ovary), Sf9 (ovary), SiHa (cervical cancer), SKBR3 (breast carcinoma), SKOV-2 (ovary carcinoma), T-47D (mammary gland), T84 (lung), U373 (glioblastoma), U87 (glioblastoma), U937 (lymphoma), VCaP (prostate), WM39 (skin), WT-49 (lymphoblastoid), YAR (B cell), embryonic cell lines, pluripotent cell lines, adult derived stem cells, reprogrammed cell lines, generic animal cell lines of any species or broadly embryonic or reprogrammed cells, patient autologous cell lines, and, in some preferred embodiments, the HT1080 human cell line is utilized. These cell lines and others are available from a variety of sources known to those with skill in the art (see, e.g., the American Type Culture Collection (ATCC) (Manassas, Va.)).

The engineering of synthetic chromosomes to express multiple genes in a biochemical or biosynthetic pathway is applicable to all of the "top down", "bottom up", engineering of minichromosomes, and induced de novo chromosome generation methods used in the art. The "bottom up" approach of synthetic chromosome formation relies on cell-mediated de novo chromosome formation following transfection of a permissive cell line with cloned α-satellite sequences, which comprise typical host cell-appropriate centromeres and selectable marker gene(s), with or without telomeric and genomic DNA. (For protocols and a detailed description of these methods see, e.g., Harrington, et al., Nat. Genet., 15:345-55 (1997); Ikeno, et al., Nat. Biotechnol., 16:431-39 (1998); Masumoto, et al., Chromosoma, 107:406-16 (1998), Ebersole, et al., Hum. Mol. Gene., 9:1623-31 (2000); Henning, et al., PNAS USA, 96:592-97 (1999); Grimes, et al., EMBO Rep. 2:910-14 (2001); Mejia, et al., Genomics, 79:297-304 (2002); and Grimes, et al., Mol. Ther., 5:798-805 (2002).) Both synthetic and naturally occurring α-satellite arrays, cloned into yeast artificial chromosomes, bacterial artificial chromosomes or P1-derived artificial chromosome vectors have been used in the art for de novo synthetic chromosome formation. The products of bottom up assembly can be linear or circular, comprise simplified and/or concatamerized input DNA with an α-satellite DNA based centromere, and typically range between 1 and 10 Mb in size. Bottom up-derived synthetic chromosomes also are engineered to incorporate nucleic acid sequences that permit site-specific integration of target DNA sequence onto the synthetic chromosome.

The "top down" approach of producing synthetic chromosomes involves sequential rounds of random and/or targeted truncation of pre-existing chromosome arms to result in a pared down synthetic chromosome comprising a centromere, telomeres, and DNA replication origins. (For protocols and a detailed description of these methods see, e.g., Heller, et al., PNAS USA, 93:7125-30 (1996); Saffery, et al., PNAS USA, 98:5705-10 (2001); Choo, Trends Mol. Med., 7:235-37 (2001); Barnett, et al., Nuc. Ac. Res., 21:27-36 (1993); Farr, et al., PNAS USA, 88:7006-10 (1991); and Katoh, et al., Biochem. Biophys. Res. Commun., 321:280-90 (2004).) "Top down" synthetic chromosomes are constructed optimally to be devoid of naturally-occurring expressed genes and are engineered to contain DNA sequences that permit site-specific integration of target DNA sequences onto the truncated chromosome, mediated, e.g., by site-specific DNA integrases.

A third method of producing synthetic chromosomes known in the art is engineering of naturally occurring minichromosomes. This production method typically involves irradiation-induced fragmentation of a chromosome containing a functional, e.g., human neocentromere possessing centromere function yet lacking α-satellite DNA sequences and engineered to be devoid of non-essential DNA. (For protocols and a detailed description of these methods see, e.g., Auriche, et al., EMBO Rep. 2:102-07 (2001); Moralli, et al., Cytogenet. Cell Genet., 94:113-20 (2001); and Carine, et a., Somat. Cell Mol. Genet., 15:445-460 (1989).) As with other methods for generating synthetic chromosomes, engineered minichromosomes can be engineered to contain DNA sequences that permit site-specific integration of target DNA sequences.

The fourth and preferred approach for production of synthetic chromosomes involves induced de novo chromosome generation by targeted amplification of specific chromosomal segments. This approach involves large-scale amplification of pericentromeric/ribosomal DNA regions situated on acrocentric chromosomes. The amplification is triggered by co-transfection of excess DNA specific to the percentric region of chromosomes, such as ribosomal RNA, along with DNA sequences that allow for site-specific integration of target DNA sequences (such as attP, attB, attL, attR or the like), and optionally a selectable marker all of which integrate into the pericentric regions of the chromosomes. (For protocols and a detailed description of these methods see, e.g., Csonka, et al., J. Cell Sci 113:3207-16 (2002); Hadlaczky, et al., Curr. Opini. Mol. Ther., 3:125-32 (2001); and Lindenbaum and Perkins, et al., Nuc. Ac. Res., 32(21):e172 (2004).) During this process, targeting to the pericentric regions of acrocentric chromosomes with co-transfected DNA induces large-scale chromosomal DNA amplification, duplication/activation of centromere sequences, and subsequent breakage and resolution of dicentric chromosomes resulting in a "break-off" satellite DNA-based synthetic chromosome containing multiple site-specific integration sites.

An integral part of the synthetic platform chromosome technology is the site-specific recombination system that allows the "loading" or placement of selected genes onto the synthetic chromosome. In preferred embodiments of the present invention, the synthetic platform chromosome comprises multiple site-specific recombination sites into each of which one or several genes of interest may be inserted. Any known recombination system can be used, including the Cre/lox recombination system using CRE recombinase from *E. coli* phage P1 (see, e.g., Sauer, Methods in Enzymology, 225:890-900 (1993) and U.S. Pat. No. 5,658,772); the FLP/FRT system of yeast using the FLP recombinase from the 2μ episome of *Saccharomyces cerevisiae* (see, e.g., Cox, PNAS U.S.A., 80:4223 (1983) and U.S. Pat. No. 5,744,336); the resolvases, including Gin recombinase of phage Mu (Maeser et al., Mol Gen Genet., 230:170-176 (1991)), Cin, Hin, αδ, Tn3; the Pin recombinase of *E. coli* (see, e.g., Enomoto et al., J Bacteriol., 6:663-668 (1983)); the R/RS system of the pSR1 plasmid of *Zygosaccharomyces rouxii* (see, e.g., Araki et al., J. Mol. Biol., 225:25-37 (1992)); site-specific recombinases from *Kluyveromyces drosophilarium* (see, e.g., Chen et al., Nucleic Acids Res., 314: 4471-4481 (1986)) and *Kluyveromyces waltii* (see, e.g., Chen et al, J. Gen. Microbiol., 138:337-345 (1992)); and other systems known to those of skill in the art; however, recombination systems that operate without the need for additional factors—or by virtue of mutation do not require additional factors—are preferred. In one exemplary embodiment, a method is provided for insertion of nucleic acids into the synthetic platform chromosome via sequence-specific recombination using the recombinase activity of the bactiophage lambda integrase.

Lambda phage-encoded integrase (designated "Int") is a prototypical member of the integrase family Int effects integration and excision of the phage into and out of the *E. coli* genome via recombination between pairs of attachment sites designated attB/attP and attL/attR. Each att site contains two inverted 9 base pair core Int binding sites and a 7 base pair overlap region that is identical in wild-type att sites. Int, like the Cre recombinase and Flp-FRT recombinase systems, executes an ordered sequential pair of strand exchanges during integrative and excisive recombination. The natural pairs of target sequences for Int, attB and attP or attL and attR are located on the same or different DNA molecules resulting in intra- or inter-molecular recombination, respectively. For example, intramolecular recombination occurs between inversely oriented attB and attP, or between attL and attR sequences, respectively, leading to inversion of the intervening DNA segment. Though wild-type Int requires additional protein factors for integrative and excisive recombination and negative supercoiling for integrative recombination, mutant Int proteins do not require accessory proteins to perform intramolecular integrative and excisive recombination in co-transfection assays in human cells (see Lorbach et al., J Mol. Biol., 25 296:1175-1181 (2000)) and are preferred for the methods of the present invention.

Delivery Vectors to Deliver Multiple Genes in the Biosynthetic Pathway

The choice of delivery vector to be used to deliver or "load" the multiple genes in the biosynthetic pathway onto the synthetic platform chromosome will depend upon a variety of factors such as the type of cell in which propagation is desired. The choice of appropriate delivery vector is well within the skill of those in the art, and many vectors are available commercially. To prepare the delivery vector, the multiple genes are inserted into a vector, typically by means of ligation of the gene sequences into a cleaved restriction enzyme site in the vector. Alternatively, the desired nucleotide sequences can be inserted by homologous recombination or site-specific recombination. Typically homologous recombination is accomplished by attaching regions of homology to the vector on the flanks of the desired nucleotide sequence (e.g., cre-lox, att sites, etc.). Nucleic acids containing such sequences can be added by, for example, ligation of oligonucleotides, or by polymerase chain reaction using primers comprising both the region of homology and a portion of the desired nucleotide sequence. Exemplary delivery vectors that may be used include but are not limited to those derived from recombinant bacteriophage DNA, plasmid DNA or cosmid DNA. For example, plasmid vectors such as pBR322, pUC 19/18, pUC 118, 119 and the M13 mp series of vectors may be used. Bacteriophage vectors may include λgt10, λgt11, λgt18-23, λZAP/R and the EMBL series of bacteriophage vectors. Cosmid vectors that may be utilized include, but are not limited to, pJB8, pCV 103, pCV 107, pCV 108, pTM, pMCS, pNNL, pHSG274, COS202, COS203, pWE15, pWE16 and the charomid 9 series of vectors. Additional vectors include bacterial artificial chromsomes (BACs) based on a functional fertility plasmid (F-plasmid), yeast artificial chromosomes (YACs), and P1-derived artificial chromsomes, DNA constructs derived from the DNA of P1 bacteriophage (PACS). Alternatively and preferably, recombinant virus vectors may be engineered, including but not limited to those derived from viruses such as herpes virus, retroviruses, vaccinia virus, poxviruses, adenoviruses, lentiviruses, adeno-associated viruses or bovine papilloma virus. BAC vectors are the preferred delivery vectors for the present invention, due to their ability to carry large amounts of nucleic acids, i.e., multiple genes. Alternatively, the multiple genes may be loaded onto the synthetic platform chromosome via sequential loading using multiple delivery vectors; that is, a first gene may be loaded onto the synthetic platform chromosome via a first delivery vector, a second gene may be loaded onto the synthetic platform chromosome via a second delivery vector, as so on. Perkins and Greene, U.S. Ser. No. 62/321,711 filed 12 Apr. 2016, describe sequential loading of multiple delivery vectors while recycling a single selectable marker.

Each of the genes from the biosynthetic pathway can be isolated and controlled from mammalian promoters, expressed either constitutively or from a regulatable promoter. A selectable marker operative in the expression host optionally may be present to facilitate selection of cells containing the delivery vector. In addition, the delivery vector may include additional elements; for example, the delivery vector may have one or two replication systems; thus allowing it to be maintained in organisms, for example in mammalian cells for expression and in a prokaryotic host for cloning and amplification.

Using lambda integrase mediated site-specific recombination—or any other recombinase-mediated site-specific recombination—the target genes are introduced or "loaded" from the delivery vector onto the synthetic platform chromosome. Because the synthetic platform chromosome contains multiple site-specific recombination sites, the multiple genes are loaded onto a single synthetic platform chromosome. The recombinase that mediates the site-specific recombination may be delivered to the cell by encoding the gene for the recombinase on the delivery vector, or purified or encapsulated recombinase protein may be delivered to a recipient cells using standard technologies. Each of the multiple target genes may be under the control of its own promoter; alternatively, the expression of the multiple target genes may be coordinately regulated via viral-based or human internal ribosome entry site (IRES) elements (see, e.g., Jackson et al., Trends Biochem Sci. 15: 477-83 (1990); and Oumard et al., Mol. Cell. Biol. 20: 2755-2759 (2000)). Additionally, using IRES type elements linked to a fluorescent marker downstream from the target genes—e.g., green, red or blue fluorescent proteins (GFP, RFP, BFP) —allows for the identification of synthetic platform chromosomes expressing the integrated target gene(s). Alternatively or in addition, site-specific recombination events on the synthetic chromosome can be quickly screened by designing primers to detect integration by PCR.

Component Delivery into the Synthetic Chromosome Production Cells

The components appropriate for synthetic chromosome production and the delivery vector(s) can be delivered to the recipient cells by any method known in the art. The terms transfection and transformation refer to the taking up of exogenous nucleic acid, e.g., an expression vector, by a host cell whether or not any coding sequences are, in fact, expressed. Numerous methods of transfection are known to the ordinarily skilled artisan, for example, by *Agrobacterium*-mediated transformation, protoplast transformation (including polyethylene glycol (PEG)-mediated transformation, electroporation, protoplast fusion, and microcell fusion), lipid-mediated delivery, liposomes, electroporation, sonoporation, microinjection, particle bombardment and silicon carbide whisker-mediated transformation and combinations thereof (see, e.g., Paszkowski, et al., EMBO J., 3:2717-2722 (1984); Potrykus, et al., Mol. Gen. Genet., 199:169-177 (1985); Reich, et al., Biotechnology, 4:1001-1004 (1986); Klein, et al., Nature, 327:70-73 (1987); U.S. Pat. No. 6,143,949; Paszkowski, et al., in *Cell Culture and Somatic Cell Genetics of Plants*, Vol. 6, Molecular Biology of Plant Nuclear Genes, (Schell and Vasil, eds., Academic Publishers 1989); and Frame, et al., Plant J., 6:941-948 (1994)); direct uptake using calcium phosphate (Wigler, et al., Proc. Natl. Acad. Sci. U.S.A., 76:1373-1376 (1979)); polyethylene glycol (PEG)-mediated DNA uptake; lipofection (see, e.g., Strauss, Meth. Mol. Biol., 54:307-327 (1996)); microcell fusion (Lambert, Proc. Natl. Acad. Sci. U.S.A., 88:5907-5911 (1991); U.S. Pat. No. 5,396,767; Sawford, et al., Somatic Cell Mol. Genet., 13:279-284 (1987); Dhar, et al., Somatic Cell Mol. Genet., 10:547-559 (1984); and McNeill-Killary, et al., Meth. Enzymol., 254: 133-152 (1995)); lipid-mediated carrier systems (see, e.g., Teifel, et al., Biotechniques, 19:79-80 (1995); Albrecht, et al., Ann. Hematol., 72:73-79 (1996); Holmen, et al., In Vitro Cell Dev. Biol. Anim., 31:347-351 (1995); Remy, et al., Bioconjug. Chem., 5:647-654 (1994); Le Bolch, et al., Tetrahedron Lett., 36:6681-6684 (1995); and Loeffler, et al., Meth. Enzymol., 217:599-618 (1993)); or other suitable methods. Methods for delivery of synthetic chromosomes also are described in U.S. application Ser. No. 09/815,979. Successful transfection is generally recognized by detection of the presence of the heterologous nucleic acid within the transfected cell, such as, for example, any visualization of the heterologous nucleic acid, expression of a selectable marker or any indication of the operation of the synthetic platform chromosome or the delivery vector within the host cell. For a description of delivery methods useful in practicing the present invention, see U.S. Pat. Nos. 5,011,776; 5,747,308; 4,966,843; 5,627,059; 5,681,713; Kim and Eberwine, Anal. Bioanal. Chem. 397(8): 3173-3178 (2010).

Visualization, Isolation, and Transfer to Recipient Immune Cells

The production and loading of the synthetic platform chromosomes of the present invention can be monitored by various methods. Lindenbaum and Perkins, et al., Nucleic Acid Research, 32(21):e172 (2004) describe the production of a mammalian satellite DNA-based Artificial Chromosome Expression (ACE) System using prior art technology. In this prior art system, conventional single-color and two-color FISH analysis and high-resolution FISH were carried out using PCR-generated probes or nick-translated probes. For detection of telomere sequences, mitotic spreads were hybridized with a commercially-obtained peptide nucleic acid probe. Microscopy was performed using fluorescent microscopy. Alternatively, Perkins and Greene, PCT/US16/17179 filed 9 Feb. 2016, describes compositions and methods to allow one to monitor formation of synthetic chromosomes in real-time via standardized fluorescent technology using two labeled tags: one labeled tag specific to endogenous chromosomes in the cell line used to produce the synthetic platform chromosomes, and one differently-labeled tag specific to a sequence on the synthetic chromosome that is to be produced.

Isolation and transfer of synthetic chromosomes typically involves utilizing microcell mediated cell transfer (MMCT) technology or dye-dependent, chromosome staining with subsequent flow cytometric-based sorting. In the MMCT technique, donor cells are chemically induced to multinucleate their chromosomes with subsequent packaging into microcells and eventual fusion into recipient cells. Establishing that the synthetic chromosomes have been transferred to recipient cells is carried out with drug selection and intact delivery of the transferred chromosome confirmed by FISH. Alternatively, flow cytometric-based transfer can be used. For flow cytometric-based transfer, mitotically arrested chromosomes are isolated and stained with DNA specific dyes and flow sorted based on size and differential dye staining. The flow-sorted chromosomes are then delivered into recipient cells via standard DNA transfection technology, and delivery of intact chromosomes is determined by FISH. In yet another alternative, in addition to the visualization and monitoring of synthetic chromosome production described in Perkins and Greene, PCT/US16/17179 filed 9 Feb. 2016, the synthetic chromosome tags can be used to isolate the synthetic chromosomes from the synthetic chromosome production cells via flow cytometry, as well as to monitor the transfer of the synthetic chromosomes into recipient cells (i.e., immune cells).

EXAMPLES

Example 1: De Novo Generation of Satellite DNA-Based Artificial Chromosome

For de novo production of synthetic chromosomes, exogenous DNA sequences were introduced into HT1080 synthetic chromosome production cell line, and, upon integration into the pericentric heterochromatic regions of acrocentric chromosomes, a large-scale amplification of the short arms of the acrocentric chromosome (rDNA/centromere region) was triggered. During the amplification event, the centromere was duplicated resulting in a dicentric chromosome with two active centromeres. Subsequent mitotic events resulted in cleavage and resolution of the dicentric chromosome, leading to a breakoff of approximately 20-120 Mb in size comprised predominantly of satellite repeat sequences with subdomains of coamplified transfected transgene that may also contain amplified copies of rDNA. The newly-generated synthetic chromosome is validated by observation of fluorescent chromosome painting (or FISH), via an endogenous chromosome tag and a synthetic chromosome tag that was engineered into the HT1080 synthetic chromosome production cell line.

The day before transfection, the HT1080 synthetic chromosome production cell line cells were split to a density of approximately 2.0 to $8.0 \times 10^4$ adherent cells into 24-well tissue culture dishes, and the vectors comprising the exogenous DNA were purified (e.g., using a Qiagen EndoFree Plasmid Maxi Kit), linearized, and the concentration of the vectors was determined for transfection. The cultured HT1080 cells were fed 3-5 hours before transfection. 225 ng of pSTV28HurDNA vector and 12.5 ng p15A7248lacEF1attPPuro vector per 24-well semiconfluent tissue culture dish was used to transfect the HT1080 cells using standard transfection reagents, e.g., ThermoFisher Lipofectamine LTX, Promega's Viafect, or Invitrogen's Calcium Phosphate Transfection Kit. The pSTV28HurDNA vector comprises the ribosomal DNA sequences. The p15A7248lacEF1attPPuro vector comprises the components for the site-specific recombination system, the LacO repeats and an ampicillin and a puromycin resistance gene. Cells were maintained for 1-3 days post-transfection at which point they were trypsinized and replated onto a 10 cm dish. Selective medium was added to the 10 cm dish at the time of plating or 1-3 days post plating. Selective conditions were maintained for 10-21 days with media changed every 2-3 days. Antibiotic resistant clones were picked when a colony reached 2-3 mm in diameter. Colonies that were well separated are preferred. Cells were removed by use of a cloning cylinder and trypsin, and transferred to a 24-well plate for expansion.

Example 2: Creating a *Saccharomyces cerevisiae* Tryptophan Pathway Delivery Vector A BLoVeL-TTS vector is used as the backbone delivery vector to insert the five genes from the *Saccharomyces cerevisiae* tryptophan pathway (Trp1-Trp5) onto the synthetic chromosome. The five tryptophan genes are separated by DNA sequences encoding either 2A peptides or IRES elements to form a single transcript containing the five genes, thereby resulting in nearly equivalent expression levels of the proteins required for tryptophan synthesis. 2A self-cleaving peptides that may be employed include but are not limited to: the porcine teschovirus-1 2A (P2A), thosea asigna virus 2A (T2A), equine rhinitis A virus 2A (E2A), foot and mouth disease virus 2A (F2A), cytoplasmic polyhedrosis virus (BmCPV 2A), and flacherie Virus 2A (BmIFV2A) (see below). Data indicates that addition of a short 3 amino acid peptide (glycine-serine-glycine) to the N-terminus of the self-cleaving peptide improves self-cleavage. Thus, this example also encompasses slight modifications to improve efficiency of the 2A self-cleaving peptide activity.

TABLE 1

| Name | GSG | 2A SEQUENCE |
|---|---|---|
| P2A | GGAAGCGGA | GCTACTAACTTCAGCCTGCTGAAGCAGGCTGGA GACGTGGAGGAGAACCCTGGACCT [SEQ ID NO. 1] |
| T2A | GGAAGCGGA | GAGGGCAGAGGAAGTCTGCTAACATGCGGTGAC GTCGAGGAGAATCCTGGACCT [SEQ ID NO. 2] |
| E2A | GGAAGCGGA | CAGTGTACTAATTATGCTCTCTTGAAATTGGCT GGAGATGTTGAGAGCAACCCTGGACCT [SEQ ID NO. 3] |
| F2A | GGAAGCGGA | GTGAAACAGACTTTGAATTTTGACCTTCTCAAG TTGGCGGGAGACGTGGAGTCCAACCCTGGACCT [SEQ ID NO. 4] |

(See, Kim, et al., PLoS ONE, 6(4), e18556. http://doi.org/10.1371/journal.pone.0018556) Internal ribosomal entry sites (IRES) elements that may be employed include but are not limited to viral and cellular IRES elements. Viral IRES elements are categorized into four types. Type I includes enterovirus (EV, PV, HRV), type II, cardiovirus (EMCV) and aphthovirus (foot-and-mouth disease virus, FMDV), type III, is used for hepatitis A virus (HAV), and the hepatitis C virus (HCV)-like IRES conforms group IV. (see Pacheco and Martinez-Salas, J Biomed Biotechnol. February 2; 2010: 458927. doi: 10.1155/2010/458927. PMID: 20150968; and Hellen and Sarnow, Genes Dev., 15(13):1593-612 (2001))

BLoVeL-TTS is digested with Eco53KI to linearize the delivery vector backbone. The five Trp genes are either synthesized or PCR amplified from *Saccharomyces cerevisiae* s288c genomic DNA using primers designed for IN-Fusion cloning (Takara) of the 5 genes and promoter of choice into the linearized BLoVeL-TTS vector.

TABLE 2

| | NCBI Reference Sequence | Size (bp) |
|---|---|---|
| Trp1 | NC_001136.10/Gene ID: 851570 | 675 |
| Trp2 | NC_001137.3/Gene ID: 856824 | 1524 |
| Trp3 | NC_001143.9/Gene ID: 853669 | 1455 |
| Trp4 | NC_001136.10/Gene ID: 851956 | 1143 |
| Trp5 | NC_001139.9/Gene ID: 852858 | 2124 |

The promoter may be selected from those found in nature or an artificially assembled promoter. The desired expression control determines whether a constitutive promoter or an inducible promoter is preferred for the specific pathway and application. For example, one could utilize a promoter that would provide a feedback mechanism to induce or suppress transcription depending on levels of specific metabolites in the cell.

The five Trp genes in the *Saccharomyces cerevisiae* biosynthetic pathway are synthesized with the following modifications: 1) Trp1, Trp2, Trp3, Trp4 genes are synthesized without a stop codon; 2) the P2A spacer is encoded upstream of the Trp2 gene and a glycine-serine-glycine spacer plus 15 bp of T2A spacer is encoded downstream of the last Trp2 amino acid codon; 3) the T2A spacer is encoded upstream of the Trp3 gene and a glycine-serine-glycine spacer plus 15 bp of E2A spacer is encoded downstream of the last Trp3 amino acid codon; 4) the E2A spacer is encoded upstream of the Trp4 gene and a glycine-serine-glycine spacer plus 15 bp of F2A spacer is encoded downstream of the last Trp4 amino acid codon; and 5) the F2A spacer is encoded upstream of the Trp5 gene and polyadenylation signal is encoded downstream of the Trp5 gene.

Figure 2:
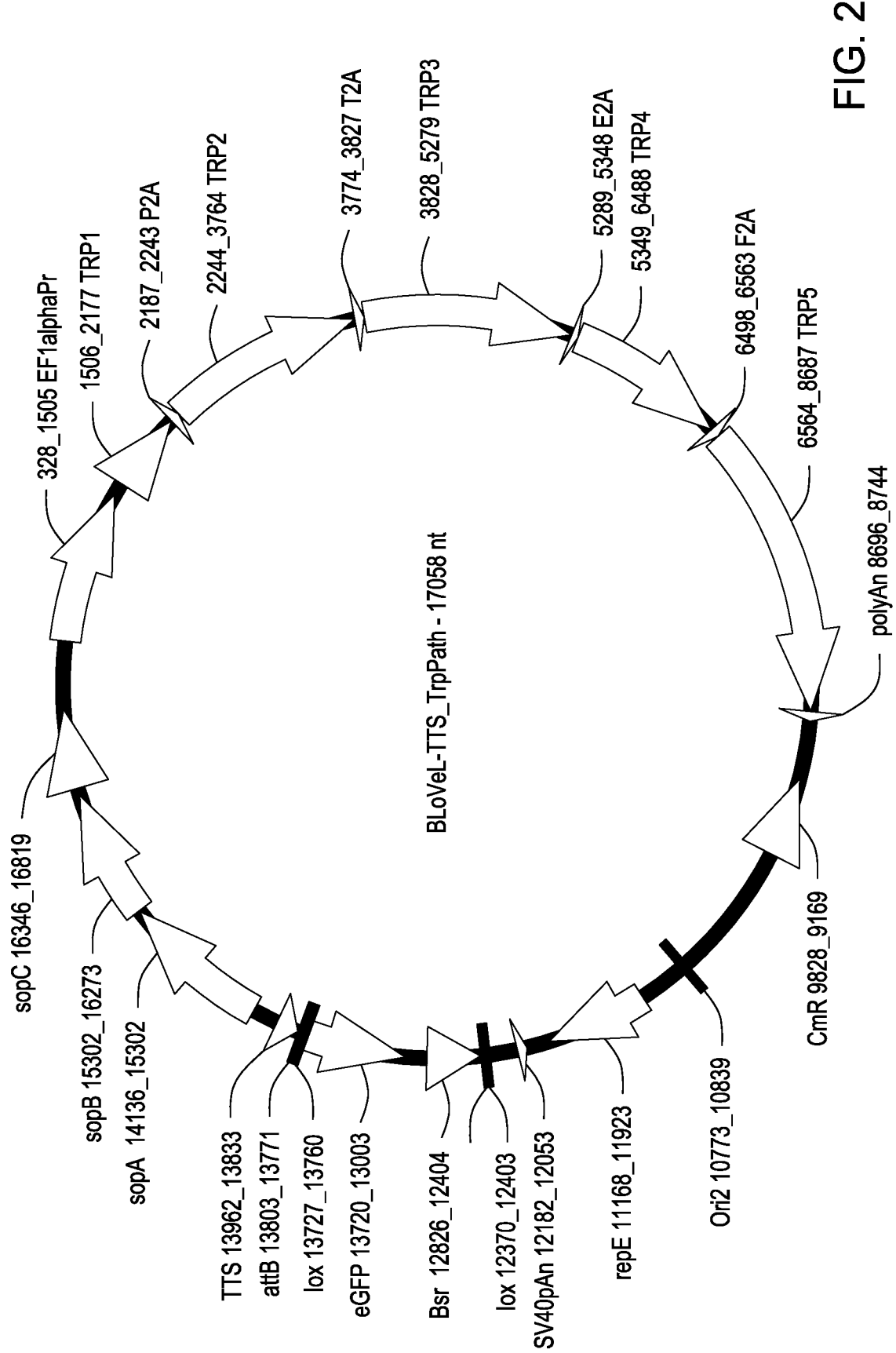
FIG. 2 illustrates one exemplary delivery vector construct, BLoVeL-TSS_TrpPath.

PCR primers are designed to PCR amplify the five synthesized DNA elements as well as the Human EF1alpha promoter (amplified from pEF1hrGFP) for IN-Fusion cloning into the linearized BLoVeL-TSS vector backbone. The resulting construct, BLoVeL-TSS_TrpPath is shown in FIG. 2. (In BLoVeL-TSS_TrpPath, the following elements are present: sopA, sopB, and sopC=plasmid partitioning proteins; SV40pAn=SV40 poly A; TTS=transcription termination signal; attB=site specific recombination site; lox=site specific recombination site; eGFP=fluorescent protein; Bsr=blasticidin resistance gene; repE=replication initiation site; Ori2=origin of replication; CmR=chloramphenicol resistance gene; polyAn=poly A; EF1alphaPr=promoter; TRP1, TRP2, TRP3 TRP4, and TRP5=tryptophan genes 1-5; P2A, T2A, E2A, and F2A=self cleaving peptides.) Once the BLoVeL-TSS_TrpPath delivery vector is constructed it is transfected into cells containing the synthetic chromosome.

Example 3: Loading the *Saccharomyces cerevisiae* Tryptophan Pathway Genes onto the Synthetic Chromosome The BLoVeL-TTS vector is used as the delivery vector to insert the five genes from the *Saccharomyces cerevisiae* tryptophan pathway (Trp1-Trp5) onto the synthetic chromosome. On day 0, the recipient cell line (e.g., HT1080) containing the synthetic chromosome (hSynC) is seeded at ~4E4 cells/well of a 24-well dish, such that the wells are ~70% confluent on Day 1. The cells are incubated overnight at 37° C., 5% $CO_2$, in appropriate medium (e.g., DMEM+ 10% FC3 for HT1080). On day 1, following the manufacturer's instructions (Fisher Scientific, Lipofectamine LTX with Plus reagent) both the delivery vector (e.g. BLoVeL-TSS_TrpPath) and the plasmid encoding the recombination protein (e.g. pCXLamIntR) are transfected into the HT1080 cells. Transfections are performed in duplicate so that a comparison of drug selection and direct cell sorting can be made. The Lipofectamine LTX is diluted in Opti-MEM medium (Gibco; 1.5 ul LTX/50 ul Opti-MEM for each well of the 24-well dish to be transfected), and 250 ng DNA is added to 50 ul diluted LTX in Opti-MEM (e.g. 125 ng BLoVeL-TSS_TrpPath plasmid and 125 ng pCXLamIntR per well). 0.25 ul PLUS reagent is added to each ~50 ul DNA-LTX-Opti_MEM sample, and each sample is incubated at room temperature for 5 minutes. The medium is then removed from the cells plated on Day 0 and fresh medium is used to replace the medium during the 5 minute incubation. DNA-lipid complexes are added to the cells and incubated at 37° C., 5% $CO_2$, in appropriate medium.

On days 2-24, drug selection is performed. The cells from one of the duplicate 24-well wells are trypsinized and transferred to a 10 cm dish with fresh medium containing drug selection (e.g., puromycin at 5 ug/ml or blasticidin at 3 ug/ml). The cells are then incubated at 37° C., 5% $CO_2$, in appropriate medium, and monitored for colony formation. The medium is replaced approximately every 72 hours. When distinct colonies are formed (approximately 10 days), each colony is isolated by a glass cylinder, trypsinized and transferred to a well of a 24-well dish. These "clones" are then expanded in culture until sufficient cells are available to place the clone in cold storage and isolate genomic DNA (approximately 2 weeks; Promega Wizard SV Genomic DNA Purification) for PCR analysis.

Alternatively, the cells in the duplicate wells can be trypsinized and placed in a 6 cm dish with fresh medium lacking drug selection, and incubated at 37° C., 5% $CO_2$, in appropriate medium. On day 3 or 4 the cells in the 6 cm dish are trypsinized and applied to a cell sorter to single cell sort fluorescent cells that have integrated the vector and are expressing the fluorescent protein on the delivery vector (e.g. GFP; BLoVeL-TSS_TrpPath). Note that the sorter identifies the in-frame GFP positive recombinants after integration onto the synthetic chromosome, which is one of the unique aspects of the methods of the invention. Integration of the delivery vector containing the gene/DNA elements of interest is identified by the production of a unique PCR product that spans the recombination site between the synthetic chromosome and the delivery vector (BLoVeL-TSS_TrpPath) using appropriate PCR primers. Negative control PCR reactions of water and host genomic DNA (e.g. HT1080) are performed in conjunction with the test genomic DNA samples. The PCR primers used to amplify the junction PCR products from BLoVeL-TSS_TrpPath vector integration are: Junction 1—Expected product size 392 bp (ACCGAGCTGCAAGAACTCTTCCTC [SEQ ID No. 5] and ctcgccgcagccgtgtaa [SEQ ID No. 6]); Junction 2—Expected product size 401 bp (gcgctaatgctctgttacaggt [SEQ ID No. 7] and GGAAAGCTGCCAGTGCCTTG [SEQ ID No. 8]).

Upon identification of candidate clones with correct junction PCR product sizes, further PCR reactions are performed to confirm presence of the DNA elements of interest originally loaded onto the delivery vector and now residing on the synthetic chromosome (e.g. TRP1, TRP2, TRP3, TRP4 and TRP5). In addition, a test of the production of tryptophan is performed, and can be determined in a number of ways. First, the cells may be tested for ability to grow in cell culture medium lacking the amino acid tryptophan with the growth of these cells compared to cells grown in cell culture medium containing tryptophan. An alternate test for tryptophan synthesis may be to assay tryptophan levels in lysed cell pellets with the Bridge-it L-Tryptophan Fluorescence Assay Kit (Mediomics, LLC). Levels of tryptophan are measured in triplicate on independent cultures carrying the TRP1, TRP2, TRP3, TRP4 and TRP5 genes and compared to cultures of cells without the BLoVeL-TSS_TrpPath containing synthetic chromosome.

Example 4: Addition of the Aromatic Amino Acid Pathway to the Tryptophan Pathway The tryptophan pathway from yeast may require the ARO pathway as well to provide the precursor for the tryptophan biosynthetic pathway in human cells. The precursor molecule that enters the tryptophan biosynthetic pathway is chorismate, which is produced by the aromatic amino acids pathway (also referred to as the shikamate pathway). In *S. cerevisiae* four genes are responsible for conversion of phosphoenol-pyruvate (PEP) and erythrose-4-phosphate (E4P) to chorismate:

TABLE 3

| Gene | NCBI Reference Sequence | Size (bp) |
| --- | --- | --- |
| AR01 | NC_001136.10/Gene ID: 851705 | 4767 |
| AR02 | NC_001139.9/Gene ID: 852729 | 1131 |

TABLE 3-continued

| Gene | NCBI Reference Sequence | Size (bp) |
| --- | --- | --- |
| AR03 | NC_001136.10/Gene ID: 851605 | 1113 |
| AR04 | NC_001134.8/Gene ID: 852551 | 1113 |

(See Braus, Microbiological Reviews, 55(3), 349-370 (1991))

Following identification of cells containing the TRP1, TRP2, TRP3, TRP4 and TRP5 genes, the selectable marker cassette (eGFP-BSR) is removed using CRE-Lox recombination. The cell line containing the synthetic chromosome is transfected with a CRE-expressing plasmid. On day 0, the cells are seeded at 2E5 cells per 6 cm cell culture dish and incubate at 37° C. with 5% $CO_2$ overnight. On day 1, the CRE-expressing plasmid (e.g. PSF-CMV-CRE-CRE Recombinase Expression Vector; Sigma Aldrich) is transfected into the cell line (containing TRP1, TRP2, TRP3, Trp4 and TRP5 genes) with Lipofectamine LTX, following the manufacturer's protocol. The Lipofectamine LTX is diluted in Opti-MEM medium (Gibco; 7.25 ul LTX/500 ul Opti-MEM for each 6-well dish to be transfected), and 1.25 ug DNA is added to 500 ul diluted LTX in Opti-MEM (e.g. PSF-CMV-CRE-CRE Recombinase Expression Vector per 6 cm dish). 1.25 ul PLUS reagent is then added to each ~500 ul DNA-LTX-Opti_MEM sample, and incubated at room temperature 5 minutes. The medium is then removed from the cells plated on Day 0 and replaced with fresh medium during the 5 minute incubation. DNA-lipid complexes are added to the cells and incubated at 37° C., 5% $CO_2$, in appropriate medium. On day 2, the CRE transfected cells from the 6 cm dish are harvested by trypsinization and gated to collect non-fluorescent cells. The non-fluorescent cells have undergone CRE-lox recombination resulting in a removal of the eGFP-BSR cassette. The non-fluorescent cells can be single cell sorted into a 96-well dish and/or bulk sorted into a tube then plated to a cell culture dish (e.g. 6 cm dish). Cells are then monitored for fluorescence as they expand in culture. Those single cell clones showing no fluorescence are expanded in culture for cold storage and genomic DNA isolation. PCR confirmation of a proper CRE-lox recombination event is determined using the following primers for BLoVeL-TSS based vectors: Lox cassette forward:

(AGCCGTGTAACCGAGCATAGtgaagcctgcttttttatactaacttga
gcgaa [SEQ ID No. 9])

Lox cassette reverse:
(CTGTTTCCTTCAGCCTGCATGGCCTTGACTAGAGGGTCGACGG
[SEQ ID No. 10])

Those candidates showing a 462 bp product indicate a proper excision of the eGFP-BSR cassette whereas a 1,819 bp product indicates no excision occurred. Candidates with the correct PCR product are further tested by PCR to confirm the presence of the DNA elements of interest.

Figure 3:
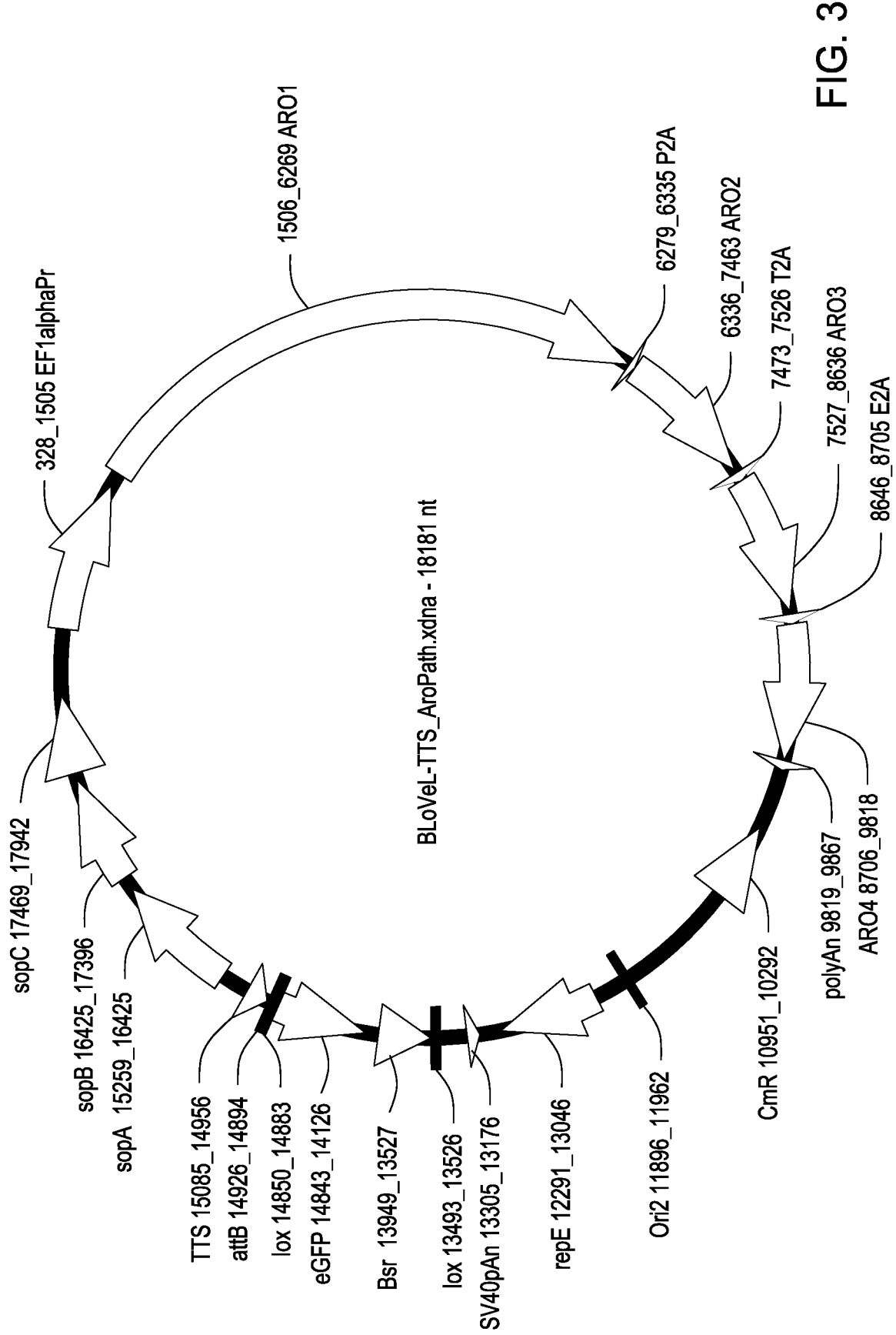
FIG. 3 illustrates another exemplary delivery vector construct, BLoVel-TSS_AroPath.

The four ARO genes in the *Saccharomyces cerevisiae* biosynthetic pathway are synthesized with the following modifications: 1) ARO1, ARO2, ARO3, genes are synthesized without a stop codon; 2) the P2A spacer is encoded upstream of the ARO2 gene and a glycine-serine-glycine spacer plus 15 bp of T2A spacer is encoded downstream of the last ARO2 amino acid codon; 3) the T2A spacer is encoded upstream of the ARO3 gene and a glycine-serine-glycine spacer plus 15 bp of E2A spacer is encoded downstream of the last ARO3 amino acid codon; and 4) the E2A spacer is encoded upstream of the ARO4 gene and polyadenylation signal is encoded downstream of the ARO4 gene. The novel synthetic polyadenylation site was copied from pGLuc-Basic_2 (NEB). PCR primers are designed to PCR amplify these four synthesized DNA elements as well as the EF1alpha promoter (amplified from pEF1hrGFP) for IN-Fusion cloning into the linearized BLoVeL-TSS delivery vector backbone. The resulting construct, BLoVeL-TSS_AroPath, is shown at FIG. 3. (In BLoVeL-TSS_AroPath, the following elements are present: sopA, sopB, and sopC=plasmid partitioning proteins; SV40pAn=SV40 poly A; TTS=transcription termination signal; attB=site specific recombination site; lox=site specific recombination site; eGFP=fluorescent protein; Bsr=blasticidin resistance gene; repE=replication initiation site; Ori2=origin of replication; CmR=chloramphenicol resistance gene; polyAn=poly A; EF1alphaPr=promoter; ARO1, ARO2, ARO3, and ARO4=aromatic amino acid genes 1-4; P2A, T2A, and E2A, =self cleaving peptides.) The BLoVeL-TSS_AroPath vector is transfected into cells containing the synthetic chromosome that has already been loaded with the TRP1, TRP2, TRP3, Trp4 and TRP5 genes.

At day 0, the recipient cell line (e.g. HT1080) containing the synthetic chromosome (hSynC) is seeded at ~4E4 cells/well of a 24-well dish, such that the wells are ~70% confluent on Day 1, and incubated overnight at 37° C., 5% CO$_2$, in appropriate medium (e.g. DMEM+10% FC3 for HT1080). On day 1, following the manufacturer's instructions (Fisher Scientific, Lipofectamine LTX with Plus reagent) both the delivery vector (e.g. BLoVeL-TSS_AroPath) and the plasmid encoding the recombination protein (e.g. pCXLamIntR) are transfected into the HT1080 cells. Transfections typically are performed in duplicate so that a comparison of drug selection and direct cell sorting can be made. The Lipofectamine LTX is diluted in Opti-MEM medium (Gibco; 1.5 ul LTX/50 ul Opti-MEM for each well of the 24-well dish to be transfected), and 250 ng DNA is added to 50 ul diluted LTX in Opti-MEM (e.g. 125 ng BLoVeL-TSS_AroPath plasmid and 125 ng pCXLamIntR per well). 0.25 ul PLUS reagent is added to each ~50 ul DNA-LTX-Opti_MEM sample, and incubated at room temperature 5 minutes. The medium is then removed from the cells plated on Day 0 and replaced with fresh medium during the 5 minute incubation. DNA-lipid complexes are added to the cells and incubated at 37° C., 5% CO$_2$, in appropriate medium.

On days 2-24, drug selection is performed. The cells from one of the duplicate 24-well wells are trypsinized and transferred to a 10 cm dish with fresh medium containing drug selection (e.g., puromycin at 5 ug/ml or blasticidin at 3 ug/ml). The cells are then incubated at 37° C., 5% CO$_2$, in appropriate medium, and monitored for colony formation. The medium is replaced approximately every 72 hours. When distinct colonies are formed (approximately 10 days), each colony is isolated by a glass cylinder, trypsinized and transferred to a well of a 24-well dish. These "clones" are then expanded in culture until sufficient cells are available to place the clone in cold storage and isolate genomic DNA (approximately 2 weeks; Promega Wizard SV Genomic DNA Purification) for PCR analysis.

Alternatively, the cells in the duplicate wells can be trypsinized and placed in a 6 cm dish with fresh medium lacking drug selection, and incubated at 37° C., 5% CO2, in appropriate medium. On day 3 or 4 the cells on the 6 cm dish are trypsinized and applied to a cell sorter to single cell sort fluorescent cells that have integrated the vector and are expressing the fluorescent protein on the targeting vector (GFP; BLoVeL-TSS_AroPath). Integration of the delivery vector containing the gene/DNA elements of interest is identified by the production of a unique PCR product that spans the recombination site between the synthetic chromosome and the delivery vector (BLoVeL-TSS_AroPath) using appropriate PCR primers. Negative control PCR reactions of water and host genomic DNA (e.g. HT1080) are performed in conjunction with the test genomic DNA samples. The PCR primers used to amplify the unique junction PCR product from BLoVeL-TSS_AroPath delivery vector integration are: Junction 1—expected product size 401 bp (gcgctaatgctctgttacaggt [SEQ ID No. 7] and GGAAAGCTGCCAGTGCCTTG [SEQ ID No. 8]). Upon identification of candidate clones with correct junction PCR product size, further PCR reactions are performed to confirm presence of the DNA elements of interest originally loaded onto the delivery vector (TRP1, TRP2, TRP3, Trp4 and TRP5 genes) and now residing on the synthetic chromosome (e.g., ARO1, ARO2, ARO3 and ARO4). Note that the second junction PCR is no longer unique with a second loading onto the synthetic chromosome: Junction shared by both BLoVeL-TSS_AroPath and BLoVeL-TSS_TrpPath targeted integrations events—expected product size 392 bp (accgagctgcaagaactcttcctc [SEQ ID No. 5] and ctcgccgcagccgtgtaa [SEQ ID No. 6]). In addition, a test of the production of chorismate is performed. This could be determined in a number of ways. For example, the cells may be tested for the ability to grow in cell culture medium lacking the amino acid tryptophan and growth compared to cells grown in cell culture medium containing tryptophan. These cells now have both the Tryptophan and Aromatic amino acid biosynthesis pathways. The latter pathway should produce the chorismate substrate for production of Tryptophan by the former pathway. An alternate test for tryptophan synthesis would be to assay tryptophan levels in lysed cell pellets with the Bridge-it L-Tryptophan Fluorescence Assay Kit (Mediomics, LLC). Levels of tryptophan are measured in triplicate on independent cultures carrying the tryptophan and compared to cultures of cells without the BLoVeL-TSS_AroPath containing synthetic chromosome as well as cultures lacking both the BLoVeL-TSS-AroPath and BLoVeL-TSS-TrpPath integration events.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention are embodied by the appended claims. In the claims that follow, unless the term "means" is used, none of the features or elements recited therein should be construed as means-plus-function limitations pursuant to 35 U.S.C. § 112, ¶16.

We claim:

1. A method for constructing a mammalian synthetic chromosome to express genes encoding enzymes involved in the synthesis of metabolites in a biosynthetic pathway in a host cell comprising:
   (a) transfecting a satellite DNA-based mammalian synthetic chromosome production cell line with synthetic chromosome production components comprising nucleic acids engineered to incorporate multiple site-specific integration sites into a satellite DNA-based synthetic platform chromosome as it is produced in the satellite DNA-based mammalian synthetic chromosome production cell line;
   (b) identifying and isolating an engineered mammalian cell carrying the satellite DNA-based mammalian synthetic platform chromosome comprising multiple site-specific integration sites produced in (a);
   (c) transfecting the isolated engineered mammalian cell of (b) carrying the synthetic platform chromosome with a delivery vector comprising at least one site-specific recombination site and multiple genes encoding multiple gene products in a first biosynthetic pathway, wherein multiple site-specific recombination sites and integration sites are selected from attachment site pairs comprising target DNA sequences attB/attP and attL/attR, or mutated versions of attP/attB and attL/attR;
   (d) activating site-specific recombination between the synthetic platform chromosome and the delivery vector using an integrase, wherein the multiple genes encoding multiple gene products in the first biosynthetic pathway are loaded onto the synthetic platform chromosome in the engineered cell to produce a satellite DNA-based mammalian synthetic chromosome expressing multiple gene products that act in concert in the first biosynthetic pathway; and
   (e) isolating a first host cell comprising the satellite DNA-based mammalian synthetic chromosome, wherein the first host cell expresses the multiple gene products that act in concert to produce metabolites in the first biosynthetic pathway.

2. The method of claim 1, wherein the multiple genes encoding multiple gene products that act in concert to produce metabolites in the first biosynthetic pathway comprise genes necessary for tryptophan biosynthesis.

3. The method of claim 2, wherein the genes necessary for tryptophan biosynthesis comprise five genes necessary for synthesis of tryptophan in *Saccharomyces cerevisiae*.

4. The method of claim 1, wherein the multiple genes are selected from the group consisting of: a) one or more genes encoding gene products that interfere with or block tumor cell ability to inhibit immune cell cycle progression, b) one or more genes encoding gene products that enhance immune cell activation and growth, and c) one or more genes encoding gene products that increase specificity of immune cells for developing tumors.

5. The method of claim 4, wherein the delivery vector comprises at least two of a), b) or c).

6. The method of claim 1, further comprising the steps of:
(f) isolating the satellite DNA-based synthetic chromosome from the first host cell of (e) expressing multiple gene-products that act in concert to produce metabolites in the first biosynthetic pathway; and
(g) transferring the satellite DNA-based synthetic chromosome of (f) to a second host cell.

7. The method of claim 6, wherein the second host cell is selected from a universal donor T-cell or a patient autologous T-cell.

8. The method of claim 1, wherein the delivery vector is a BAC.

9. The method of claim 1, further comprising the steps of:
(f) transfecting the first host cell comprising the mammalian satellite DNA-based synthetic chromosome expressing the multiple gene products that act in concert to produce metabolites in the first biosynthetic pathway with a second delivery vector comprising at least one site-specific recombination site and multiple genes encoding multiple gene products in a second biosynthetic pathway, wherein multiple site-specific integration sites and recombination sites are selected from attachment site pairs consisting of target DNA sequences attB/attP and attL/attR, or mutated versions of attB/attP and attL/attR;
(g) activating site-specific recombination between the mammalian satellite DNA-based synthetic chromosome expressing the multiple gene products that act in concert to produce metabolites in the first biosynthetic pathway and the second delivery vector using an integrase, wherein the multiple genes encoding multiple gene products in the second biosynthetic pathway are loaded onto the mammalian satellite DNA-based synthetic chromosome to produce a second satellite DNA-based mammalian synthetic chromosome expressing the multiple gene products in both the first biosynthetic pathway and the second biosynthetic pathway; and
(h) isolating a second host cell comprising the second satellite DNA-based mammalian synthetic chromosome expressing the multiple gene products in both the first biosynthetic pathway and the second biosynthetic pathway.

10. The method of claim 9, further comprising the steps of:
(i) isolating the second satellite DNA-based mammalian synthetic chromosome expressing the multiple gene products in both the first biosynthetic pathway and the second biosynthetic pathway; and
(j) transferring the second satellite DNA-based mammalian synthetic chromosome expressing the multiple gene products in both the first biosynthetic pathway and the second biosynthetic pathway to a third host cell.

11. The method of claim 9, wherein the second host cell is selected from a universal donor T-cell or a patient autologous T-cell.

12. A method for constructing a mammalian synthetic chromosome to express genes encoding enzymes involved in the synthesis of metabolites in a biosynthetic pathway in a host immune cell comprising:
(a) transfecting a satellite DNA-based mammalian synthetic chromosome production cell line with synthetic chromosome production components comprising nucleic acids engineered to incorporate multiple site-specific integration sites into a satellite DNA-based synthetic platform chromosome as it is produced in the satellite DNA-based mammalian synthetic chromosome production cell line;
(b) identifying and isolating an engineered mammalian cell carrying the satellite DNA-based mammalian synthetic platform chromosome comprising multiple site-specific integration sites produced in (a);
(c) transfecting the isolated engineered mammalian cell of (b) carrying the synthetic platform chromosome with a delivery vector comprising at least one site-specific recombination site and multiple genes encoding multiple gene products in a first biosynthetic pathway, wherein multiple site-specific recombination sites and integration sites are selected from attachment site pairs comprising target DNA sequences attB/attP and attL/attR, or mutated versions of attP/attB and attL/attR;
(d) activating site-specific recombination between the satellite DNA-based synthetic platform chromosome and the delivery vector using an integrase, wherein the multiple genes encoding multiple gene products in the first biosynthetic pathway are loaded onto the synthetic platform chromosome in the engineered cell to produce a satellite DNA-based mammalian synthetic chromosome expressing multiple gene products that act in concert in the first biosynthetic pathway; and
(e) isolating a first host cell comprising the satellite DNA-based mammalian synthetic chromosome, wherein the first host cell expresses the multiple gene products in the first biosynthetic pathway;
(f) isolating the satellite DNA-based mammalian synthetic chromosome expressing the multiple gene products that act in concert to produce metabolites in the first biosynthetic pathway; and
(g) transferring the satellite DNA-based mammalian synthetic chromosome to a recipient host immune cell.

* * * * *